United States Patent [19]
Chou et al.

[11] Patent Number: 5,453,499
[45] Date of Patent: Sep. 26, 1995

[54] PROCESS FOR PREPARING ALPHA-ANOMER ENRICHED 1-HALO-2-DEOXY-2,2-DIFLUORO-D-RIBOFURANOSYL DERIVATIVES

[76] Inventors: Ta-Sen Chou, 11338 Bayhill Way, Indianapolis, Ind. 46217; Charles D. Jones, 223 E. Brunswick Ave., Indianapolis, Ind. 46227; Thomas E. Mabry, 8104 Hi-Vu Dr., Indianapolis, Ind. 46227

[21] Appl. No.: 99,014

[22] Filed: Jul. 29, 1993

Related U.S. Application Data

[63] Continuation-in-part of Ser. No. 902,306, Jun. 22, 1992, abandoned.

[51] Int. Cl.⁶ .................................. C07H 5/02; C07H 1/00
[52] U.S. Cl. ........................ 536/122; 536/124; 549/475; 549/476
[58] Field of Search .......................... 536/122, 124; 549/475, 476

[56] References Cited

U.S. PATENT DOCUMENTS

| | | | |
|---|---|---|---|
| 4,526,988 | 7/1985 | Hertel | 549/313 |
| 4,965,374 | 10/1990 | Chou et al. | 549/313 |
| 5,252,756 | 10/1993 | Chou et al. | 549/476 |
| 5,256,797 | 10/1993 | Chou et al. | 549/476 |
| 5,256,798 | 10/1993 | Chou et al. | 549/476 |

OTHER PUBLICATIONS

Cancer Research, vol. 49, issued 01 Aug. 1989, Tietze et al, "Proton14 mediated Liberation of Aldophosphamide from a Nontoxic Prodrug: A Strategy for Tumor–Selective Activation of Cytocidal Drugs" pp. 4179–4184.

*Primary Examiner*—Michael G. Wityshyn
*Assistant Examiner*—Everett White
*Attorney, Agent, or Firm*—Robert A. Conrad; David E. Boone

[57] ABSTRACT

A stereoselective process for preparing an alpha-anomer enriched 1-α-halo-2-deoxy-2,2-difluoro-D-ribofuranosyl derivatives involving contacting a 3,5-hydroxy protected-2-deoxy-2,2-difluoro-D-ribofuranosyl-1-β-sulfonate with a halide source in an inert solvent.

17 Claims, No Drawings

PROCESS FOR PREPARING ALPHA-ANOMER ENRICHED 1-HALO-2-DEOXY-2,2-DIFLUORO-D-RIBOFURANOSYL DERIVATIVES

CROSS REFERENCE TO RELATED APPLICATIONS

This application is a Continuation-In-Part of application Ser. No. 07/902,306, filed Jun. 22, 1992, now abandoned.

BACKGROUND OF THE INVENTION

1. Field of the Invention

This invention pertains to a process for making alpha-anomer enriched 3,5-hydroxy protected-1-halo-2-deoxy-2,2-difluoro-D-ribofuranosyl derivatives.

2. State of the Art

Fluorine substitution has been investigated extensively in drug research and biochemistry as a means of enhancing the biological activity and increasing the chemical or metabolic stability of nucleosides. The replacement of a hydrogen by fluorine in a bioactive molecule is expected to cause minimal steric pertubations with respect to the molecule's mode of binding to receptors or enzymes and aid in overcoming the chemical and enzymatic instability problems of nucleosides. Nucleosides are typically synthesized by coupling a ribofuranosyl derivative with a purine or pyrimidine nucleobase. Synthetic reactions leading to many nucleosides involve stereochemical inversion of the ribofuranosyl configuration at the anomeric position. When applied to making alpha-anomer enriched starting material, this inversion provides increased amounts of biologically important beta-anomer nucleosides.

U.S. Pat. No. 4,526,988 describes a process for making 3,5-hydroxy protected-1-halo-2-deoxy-2,2-difluoro-D-ribofuranosyl derivatives by displacing the C1-acetate of 3,5-bis(t-butyldimethylsilyloxy) 2-deoxy-2,2-difluororibofuranose with a hydrogen halide such as hydrogen bromide or hydrogen chloride at −50° C. to about 0° C. The resulting compound is then coupled with a purine or pyrimidine base to form an anomeric mixture of nucleosides.

There continues to be a need for a stereoselective process for preparing alpha-anomer enriched 1-halo-2-deoxy-2,2-difluror-D-ribofuranosyl derivatives useful in stereoselective coupling reactions used to prepare anti-neoplastic and/or antiviral nucleoside agents.

Accordingly, one object of the present invention is to provide a stereoselective process for preparing alpha-anomer enriched 3,5-hydroxy protected-1-halo-2-deoxy-2,2-difluoro-D-ribofuranosyl derivatives.

Another object of the present invention is to provide a stereoselective process for preparing alpha-anomer enriched 3,5-hydroxy protected-1-halo-2-deoxy-2,2-difluoro-D-ribofuranosyl derivatives in high yields.

SUMMARY OF THE INVENTION

The present invention is a stereoselective process for preparing an alpha-anomer enriched ribofuranosyl derivative of the formula

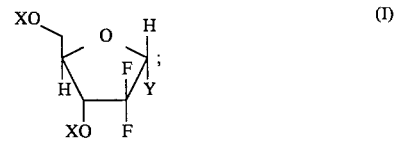

wherein each X is independently selected from hydroxy protecting groups and Y is halo; comprising contacting a 3,5-hydroxy protected-2-deoxy-2,2-difluoro-D-ribofuranosyl-1-β sulfonate with a halide source in an inert solvent.

DETAILED DESCRIPTION OF THE INVENTION

Throughout this document, all temperatures are in degrees Celsius, all proportions, percentages and the like, are in weight units and all mixtures are in volume units, except where otherwise indicated. Anomeric mixtures are expressed as a weight/weight ratio or as a percent. The term "lactol" alone or in combination refers to 2-deoxy-2,2-difluoro-D-ribofuranose. The terms "halo" or "halide" alone or in combination refer to chloro, iodo, fluoro and bromo or their anionic form, respectively. The term "alkyl" alone or in combination refers to straight, cyclic and branched chain aliphatic hydrocarbon groups which preferably contain up to 7 carbon atoms, such as, methyl, ethyl, n-propyl, isopropyl, n-butyl, t-butyl, n-pentyl, n-hexyl, 3-methylpentyl groups and the like or substituted straight, cyclic and branched chain aliphatic hydrocarbons such as chloroethane, 1,2-dichloroethane and the like. The term "alkoxy" alone or in combination refers to compounds of the general formula RO; wherein R is an alkyl as defined above. The term "aryl" alone or in combination refers to carbocyclic or hetero cyclic groups such as phenyl, naphthyl, thienyl and substituted derivatives thereof. The term "aromatic" alone in combination refers to benzene-like structures containing (4n+2) delocalized π electrons. The term "sulfonate" alone or in combination refers to compounds of the general formula $BSO_3$, wherein B is a substituted alkyl, unsubstituted alkyl, substituted aryl, or unsubstituted aryl. The term "substituted" alone or in combination refers to the replacement of hydrogen or a common moiety by one or more of the groups selected from cyano, halo, carboalkoxy, aryl, nitro, alkoxy, alkyl, halo alkyl, and dialkyl amino. The phrase "anomer enriched" alone or in combination refers to an anomeric mixture wherein the ratio of a specified anomer is greater than 1:1 and includes a substantially pure anomer.

In accordance with the present process 3,5-hydroxy protected-2-deoxy-2,2-difluoro-D-ribofuranosyl-1-β-sulfonate is contacted with a halide source in an inert solvent to prepare a compound of formula I.

The preparation of 3,5-hydroxy protected-2-deoxy-2,2-difluoro-D-rebofuranosyl-1-β-sulfonate starting materials is described for example in U.S. Pat. No. 5,252,756, which teaches 3,5-hydroxy protected-2-deoxy-2,2-difluoro-D-ribofuranosyl-1-β-arylsulfonates wherein the arylsulfonates are benzenesulfonate, substituted arylsulfonates such as toluenesulfonate (p-bromobenzene)sulfonate, (p-chlorobenzene)sulfonate, (p-methylbenzene)sulfonate and (p-fluorobenzene)sulfonate.

As for 3,5-hydroxy protected-2-deoxy-2,2-difluoro-D-ribofuranosyl-1-β-alkylsulfonates, they may be prepared by separating a 1:1 anomeric mixture of 3,5-hydroxy protected-2-deoxy-2,2-difluoro-D-ribofuranosyl-1- alkylsulfonates by selective crystallization or column chromatography, as described by Chou, et al. in Synthesis, pp. 565–70 (Jun. 1992).

In the case of 3,5-hydroxy protected-2-deoxy-2,2-difluoro-D-ribofuranosyl-1-β-trifluoromethanesulfonate and 3,5-hydroxy protected-2-deoxy-2,2-difluoro-D-ribofuranosyl-1-β-2,4-dinitrobenzene sulfonate, trifluoromethanesulfonyl halide and 2,4-dinitrobenzene sulfonyl halide, respectively, are used as sulfonating reagents in the presence of a tertiary amine base, such as triethylamine. A beta-anomer enriched mixture of the 3,5-hydroxy protected-2-deoxy-2,2-difluro-D-ribofuranosyl-1-sulfonate is formed. These sulfonates are very reactive and react in situ with the halide ion generated in the reaction mixture as a by-product. The product from the in situ reaction is a alpha-anomer enriched 1-halo-2-deoxy-2,2-difluororibofuranosyl derivative.

The trifluoromethanesulfonyl halide sulfonating reagent can be replaced by other fluorinated alkyl sulfonyl halides, such as nanoflyl halide (e.g. $C_4F_9SO_2$-halide) and octaflyl halide (e.g. $C_4F_8HSO_2$-halide). Likewise, the 2,4-dinitrobenzenesulfonyl halide sulfonating reagent can be replaced by a monosubstituted nitroarylsulfonyl halide.

Suitable halide sources useful in the present process may be selected from the group consisting of tetraalkylammonium halides, trialkylammonium halides, lithium halides, cesium halides, sodium halides and potassium halides; preferred are tetraalkylammonium halides such as tetrabutylammonium iodide and tetrabutylammonium bromide, tetramethylammonium bromide, tetramethylammonium chloride, tetramethylammonium (fluoride,2-hydrate), tetraethylammonium bromide, tetraethylammonium chloride, tetraethylammonium(fluoride,2-hydrate), and trialkylammonium halides such as triehtylamine hydrochloride, triethylamine hydrobromide, triethylamine hydroiodide, tricaprylmethylammonium chloride; and pyridine hydrochloride. The halide source, except when generated in situ, is employed in at least equimolar amount, relative to the amount of hydroxy protected 2-deoxy-2,2-difluoro-D-ribofuranose-1-β-sulfonate employed, and more preferably is from about 1.05 molar equivalents to about 5 molar equivalents.

The solvent may be any solvent that is inert to the reaction mixture and is preferably selected from the group consisting of acetonitrile, N,N-dimethylformamide, dioxane, aryl halides such as chlorobenzene or bromobenzene, dialkyl ethers such as dibutyl ether, esters such as ethyl acetate, ketones such as acetone or 2-butanone, alkyl halides such as dichloromethane or 1,2-dichloroethane, dimethylsulfoxide, tetrahydrofuran, N,N-dimethylpropyleneurea, N-methylpyrrolidinone, and mixtures thereof. The preferred solvent depends on the halide source selected. For example, when a tetraalkylammonium halide is used, acetonitrile is preferably employed as the solvent.

The hydroxy protecting groups (X) are known in the art and are described in Chapter 3 of Protective Groups in Organic Chemistry, McOmie Ed., Plenum Press, New York (1973), and Chapter 2 of Protective Groups in Organic Synthesis, Green, John, J. Wiley and Sons, New York (1981); preferred are ester forming groups such as formyl, acetyl, substituted acetyl, propionyl, butynyl, pivaloyl, 2-chloroacetyl, benzoyl, substituted benzoyl, phenoxycarbonyl, methoxyacetyl; carbonate derivatives such as phenoxycarbonyl, t-butoxycarbonyl ethoxycarbonyl, vinyloxycarbonyl, 2,2,2-trichloroethoxycarbonyl and benzyloxycarbonyl; alkyl ether forming groups such as benzyl, diphenylmethyl, triphenylmethyl, t-butyl, methoxymethyl, tetrahydropyranyl, allyl, tetrahydrothienyl, 2-methoxyethoxy methyl; and silyl ether forming groups such as trialkylsilyl, trimethylsilyl, isopropyldialkylsilyl, alkyldiisopropylsilyl, triisopropylsilyl, t-butyldialkylsilyl and 1,1,3,3,-tetraisopropyldisloxanyl; carbamates such as N-phenylcarbamate and N-imidazoylcarbamate; however more preferred are benzoyl, mono-substituted benzoyl and disubstituted benzoyl, acetyl, pivaloyl, triphenylmethyl ethers, and silyl ether forming groups, especially t-butyldimethylsilyl; while most preferred is benzoyl.

The temperature employed in the present process is from about room temperature to the reflux temperature of the mixture. The process is preferably carried out under atmospheric pressure and is substantially complete in about 5 minutes to about 24 hours.

In another embodiment of the present process, a small amount of catalyst is added along with the halide source to increase the nucleophilicity of the halide source. The catalyst may be selected from the group consisting of crown ethers such as 18-Crown-6, 15-Crown-5, and 12-Crown-4.

The progress of the present process may be followed using high pressure liquid chromatography (HPLC) or nuclear magnetic resonance (NMR) spectroscopy.

The following examples illustrate specific aspects of the present process and are not intended to limit the scope thereof in any respect and should not be so construed.

Example 1

Preparation of alpha-anomer enriched 1-α-iodo-2-deoxy-2,2-difluoro-D-ribofuranosyl-3,5-dibenzoate To 1 g of 2-deoxy-2,2-difluoro-D-ribofuranosyl-3,5-dibenzoyl-1-β-(p-bromobenzene) sulfonate were added 80 ml of tetrahydrofuran and 80 ml of tetrabutylammonium iodide. After about 3.5 hours at reflux the titled compound was formed in an alpha to beta ratio of 10:1, as determined by proton NMR spectroscopy.

To isolate the alpha-anomer the reaction mixture was cooled and diluted with dichloromethane and water. The layers were separated and the organic layer was washed with 1N HCl, sodium carbonate, saturated sodium chloride and water then dried over magnesium sulfate. The resulting solution was concentrated to an oily residue and chromatographed (silica gel, toluene/hexanes 2:1) to give 302 mg of the titled product. The yield of the titled compound was 45 percent. FDMS 489(m+2), 361(m-127), QE 300 $^1$HNMR(CDCl$_3$) δ=8.12(m, 4H, Ar-o), 7.72 -7.4 (m, 6H, Ar-m and p), 6.92 (d, 1H, 1-H), 5.60(dd, 1H, 3-H), 4.91-4.62($\overline{m}$, 3H, 4-H and 5-H).

Example 2

Preparation of alpha-anomer enriched 1-β-bromo-2-deoxy-2,2-difluoro-D-ribofuranosyl-3,5-dibenzoate To 0.39 g of 2-deoxy-2,2-difluoro-D-ribofuranosyl-3,5-dibenzolyl-1-β-(p-bormobenzene) sulfonate were added 0.086 g of potassium bromide and 8 ml of N,N-dimethylformamide over 0.661 g of 4 angstrom sieves. After about 16 hours at 20° C. the titled compound was formed in an alpha to beta ratio of 10:1, as determined by proton NMR spectroscopy.

To isolate the alpha-anomer the reaction mixture was diluted with dichloromethane and water. The layers were separated and the organic layer was washed with 0.2 M lithium chloride and water then dried over magnesium sulfate. The resulting solution was concentrated to give 234 mg of an oily residue which was substantially the titled product. A sample of the residue was chromotographed (silica gel, toluene) to give a colored oil. FDMS 442 (m+1); Elemental Analysis: (Calc.) C: 51.72, H: 3.43, Br: 18.11; (Actual) C: 51.93, H: 3.48, Br: 18.33. QE 300 $^1$HNMR(CDCl$_3$) δ=8.12 (m, 4H, Ar-o), 7.7-7.38(m, 6H, Ar-m and p), 6.55(d, 1H, 1-H), 5.60(dd, 1H, 3-H), 4.89-4.65(m, 3H, 4-H and 5-H).

Example 3

Preparation of alpha-anomer enriched 1-α-bromo-2-deoxy-2,2-difluoro-D-ribofuranosyl-3,5-dibenzoate To 7.2 g of 2-deoxy-2,2-difluoro-D-ribofuranosyl-3,5-dibenzoyl-1-β-(p-bromobenzene) sulfonate were added 540 ml of tetrahydrofuran and 3.65 g of tetrabutylammonium bromide. After about 2 hours at reflux the titled compound was formed in an alpha to beta ratio of 9:1, as determined by proton NMR spectroscopy.

To isolate the alpha-anomer the reaction mixture was diluted with dichloromethane and water. The layers were separated and the organic layer was washed with 1N HCl, sodium carbonate, saturated sodium chloride and water then dried over magnesium sulfate. The resulting solution was concentrated to an oily residue and chromatographed (silica gel, toluene/hexanes 2:1) to give 4.35 g of a slightly colored oil. The yield of the titled compound was 87 percent. FDMS 442(m+1); Elemental Analysis: (Calc.) C: 51.72, H: 3.43, Br: 18.11; (Actual) C: 52.79, H: 3.53, Br: 18.57.

Example 4

Preparation of alpha-anomer enriched 1-α-iodo-2-deoxy-2,2-difluoro-D-ribofuranosyl-3,5-dibenzoate To 6 g of 2-deoxy-2,2-difluoro-D-ribofuranosyl-3,5-dibenzoyl-1-β-(p-bromobenzene) sulfonate were added 250 ml of acetonitrile and 5.56 g of tetrabutylammonium iodide. After about 22 hours at 45° C. the titled compound was formed in an alpha to beta ratio of 10:1, as determined proton NMR spectroscopy.

To isolate the alpha-anomer the reaction mixture was diluted with diethyl ether and water. The layers were separated and the organic layer was washed with 1N HCl, sodium carbonate, saturated sodium chloride and water then dried over magnesium sulfate. The resulting solution was concentrated to an oily residue and chromatographed (silica gel, toluene/hexanes 2:1) to give 4.02 g of a slightly colored oil. The yield of the titled compound was 82 percent. Elemental Analysis: (Calc.) C: 46.74, H: 3.10; (Actual) C: 46.98, H: 3.22.

Example 5

Preparation of alpha-anomer 1-α-fluoro-2-deoxy-2,2-difluoro-D-ribofuranosyl-3,5-dibenzoate To 200 mg of 2-deoxy-2,2-difluoro-D-ribofuranosyl-3,5-dibenzoyl-1-β-(p-toluene) sulfonate were added 5 ml of tetrahydrofuran and 0.376 ml of tetrabutylammonium fluoride. After about 17 hours at 50° C. the titled compound was formed, as determined proton NMR spectroscopy.

To isolate the alpha-anomer the reaction mixture was diluted with dichloromethane and water. The layers were separated and the organic layer was washed with 1N HCl, sodium carbonate, saturated sodium chloride and water then dried over magnesium sulfate. The resulting solution was concentrated to an oily residue and chromatographed (silica gel, toluene/hexanes 2:1) to give 154 mg of a yellow oil. The yield of the titled compound was 42 percent.

Example 6

Preparation of alpha-anomer enriched 1-α-chloro-2-deoxy-2,2-difluoro-D-ribofuranosyl-3,5dibenzoate.

100 mg of 2-deoxy-2,2-difluoro-D-ribofuranose-3,5-dibenzoate were dissolved in 10 ml of dichloromethane and 55 µl of triethylamine and stirred. The reaction mixture was cooled and 31 µl of trifluoromethane sulfonyl chloride were added and the cooling stopped. After about 2 hours the titled compound was formed in an alpha to beta ratio of 3.6:1, as determined by proton NMR spectroscopy.

Example 7

Preparation of alpha-anomer enriched 1-α-chloro-2-deoxy-2,2-difluro-D-ribofuranosyl-3,5-dibenzoate.

100 mg of 2-deoxy-2,2-difluoro-D-ribofuranose-3,5-dibenzoate are dissolved in 10 ml of dichloromethane and 55 µl of triethylamine and stirred. The reaction mixture is cooled and 31 µl of 2,4-dinitrobenzenesulfonyl chloride added and the cooling stopped. After about 2 hours the title compound will form in an alpha to beta ratio of about 9:1, which can be determined by proton NMR spectroscopy.

The present invention has been described in detail, including the preferred embodiments thereof. However, it will be appreciated that those skilled in the art, upon consideration of the present disclosure, may make modifications and/or improvements on this invention that fall within the scope and spirit of the invention as set forth in the following claims.

What is claimed is:

1. A stereoselective process for preparing an alpha-anomer enriched ribofuranosyl derivative of the formula

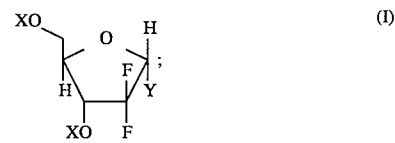

wherein each X is independently selected from hydroxy protecting groups and Y is halo; comprising contacting a 3,5-hydroxy protected-2-deoxy-2,2-difluoro-D-ribofuranosyl-1-β sulfonate with a halide source in an inert solvent.

2. The process of claim 1 wherein the halide source is selected from the group consisting of tetraalkylammonium halides, trialkylammonium halides, lithium halides, sodium halides, cesium halides and potassium halides.

3. The process of claim 2 wherein the halide source is selected from tetraalkylammonium halides.

4. The process of claim 3 wherein the halide source is selected from tetrabutylammonium bromide, tetrabutylammonium iodide and tetrabutylammonium fluoride.

5. The process of claim 1 wherein the amount of halide source is about 1 molar equivalent to about 5 molar equivalents.

6. The process of claim 1 wherein the solvent is selected from the group consisting of acetonitrile, dimethylformamide, tetrahydrofuran, N,N'-dimethylpropyleneurea, dichloromethane, and mixtures thereof.

7. The process of claim 6 wherein the solvent is selected from the group consisting of tetrahydrofuran, acetonitrile, and mixtures thereof.

8. The process of claim 1 wherein Y is iodo comprising contacting a 2-deoxy-2,2-difluoro-D-ribofuranosyl-1-β-sulfonate with tetrabutylammonium iodide in acetonitrile.

9. The process of claim 1 wherein Y is bromo comprising contacting a 2-deoxy-2,2-difluoro-D-ribofuranosyl-3,5-dibenzoyl-1-β-sulfonate with potassium bromide in dimethylformamide.

10. The process of claim 1 wherein Y is iodo comprising contacting a 2-deoxy-2,2-difluoro-D-ribofuranosyl-3,5-dibenzoyl-1-β-sulfonate with tetrabutylammonium iodide in tetrahydrofuran.

11. The process of claim 1 wherein Y is bromo comprising contacting a 2-deoxy-2,2-difluoro-D-ribofuranosyl-3,5-dibenzoyl-1-β-sulfonate with tetrabutylammonium bromide in acetonitrile.

12. The process of claim 1 wherein Y is fluoro comprising contacting a 2-deoxy-2,2-difluoro-D-ribofuranosyl-3,5-dibenzoyl-1-β-sulfonate with tetrabutylammonium fluoride in tetrahydrofuran.

13. The process of claim 1 wherein the β-sulfonate is 2-deoxy-2,2-difluoro-D-ribofuranosyl-3,5-dibenzoyl-1-β-(p-bromobenzene) sulfonate.

14. The process of claim 1 wherein the β-sulfonate is 2-deoxy-2,2-difluoro-D-ribofuranosyl-3,5-dibenzoyl-1-β-(p-toluene) sulfonate.

15. The process of claim 1 wherein the β-sulfonate is 2-deoxy-2,2-difluoro-D-ribofuranosyl-3,5-dibenzoyl-1-β-trifluromethanesulfonate.

16. The process of claim 1 wherein the β-sulfonate is 2-deoxy-2,2-difluoro-D-ribofuranosyl-3,5-dibenzoyl-1-β-2,4-dinitrobenzenesulfonate.

17. The process of claim 1 further comprising adding a catalyst selected from crown ethers.

* * * * *